(12) United States Patent
Suh et al.

(10) Patent No.: US 9,687,482 B2
(45) Date of Patent: Jun. 27, 2017

(54) STABLE PHARMACEUTICAL COMPOSITION COMPRISING SOLIFENACIN, AND METHOD FOR PREPARING THE SAME

(71) Applicant: CJ HEALTHCARE CORPORATION, Seoul (KR)

(72) Inventors: Young Hee Suh, Seoul (KR); Young Dae Cho, Osan-si (KR); Chun Seon Lyu, Yongin-si (KR); Mi Young Yoon, Cheonan-si (KR); Ha Yong Choi, Yongin-si (KR); Sung Kyun Han, Hwaseong-si (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 14/608,560

(22) Filed: Jan. 29, 2015

(65) Prior Publication Data

US 2015/0216856 A1   Aug. 6, 2015

(30) Foreign Application Priority Data

Feb. 3, 2014   (KR) .................. 10-2014-0012121

(51) Int. Cl.

| | | |
|---|---|---|
| *A61K 31/4725* | (2006.01) | |
| *A61K 31/439* | (2006.01) | |
| *A61K 47/10* | (2017.01) | |
| *A61K 47/38* | (2006.01) | |
| *A61K 9/20* | (2006.01) | |

(52) U.S. Cl.
CPC ........ *A61K 31/4725* (2013.01); *A61K 9/2054* (2013.01); *A61K 9/2095* (2013.01); *A61K 31/439* (2013.01); *A61K 47/10* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 7,070,811 B2 | 7/2006 | Murphy et al. | |
| 8,992,976 B2 | 3/2015 | Schulze Nahrup et al. | |
| 2010/0137358 A1* | 6/2010 | Kharwade .............. | A61K 9/146 514/305 |
| 2010/0273825 A1 | 10/2010 | Wako et al. | |

FOREIGN PATENT DOCUMENTS

| | | |
|---|---|---|
| CN | 104739789 A | 7/2015 |
| EP | 2 018 850 A1 | 1/2009 |
| EP | 2 500 013 A1 | 9/2012 |
| KR | 1020070010132 A | 1/2007 |
| KR | 1020070098889 A | 10/2007 |
| KR | 1020120093500 A | 8/2012 |
| WO | 2008/128028 A2 | 10/2008 |
| WO | 2009/012987 A1 | 1/2009 |
| WO | 2010/097243 A2 | 9/2010 |

* cited by examiner

*Primary Examiner* — Samantha Shterengarts
(74) *Attorney, Agent, or Firm* — Seed IP Law Group LLP

(57) ABSTRACT

The present invention relates to a solifenacin preparation containing solifenacin or a pharmaceutically acceptable salt thereof, an antioxidant, and a binder, which is manufactured via direct compression. Compared to the preparations manufactured via conventional wet granulation process, the preparation of the present invention can be manufactured by a simplified process such as direct compression, and has improved content uniformity, mixing degree, etc., even when the preparation is manufactured by high speed tableting.

10 Claims, 3 Drawing Sheets

STABLE PHARMACEUTICAL COMPOSITION COMPRISING SOLIFENACIN, AND METHOD FOR PREPARING THE SAME

TECHNICAL FIELD

The present invention relates to a stable preparation containing solifenacin, and a method of manufacturing the same.

BACKGROUND ART

Solifenacin is a compound represented by Chemical Formula 1 below and is reported to have an excellent selective antagonistic action against muscarinic M3 receptors.

[Chemical Formula 1]

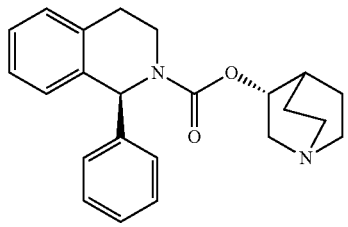

Meanwhile, although solifenacin or a pharmaceutically acceptable salt thereof may be stable in the state of a raw material, there is a problem with the drug in that it decomposes with time due to various factors involved in the process of manufacturing it into a final product. As a representative example, an amorphous form of solifenacin succinate is generated during the process of wet granulation and easily oxidized within a short period. In particular, the main degradation product (an oxidized form of solifenacin succinate) has been reported to be the major cause of the decomposition problems of the main drug. That is, it is difficult to develop a desirable formulation and process due to drug instability problems which may occur, depending on various process conditions such as reaction temperature, pH, reaction time, order of mixing, etc., or by interactions occurring when excipients, binders, lubricants, etc. are combined and come in contact with the active ingredient, depending on the characteristics of exipients, etc.

Additionally, the cohesiveness of solifenacin or a pharmaceutically acceptable salt thereof complicates the formulation process. KR Patent Application Publication No. 10-2007-0010132 discloses that it is preferred that any formulations containing solifenacin or a pharmaceutically acceptable salt thereof be manufactured via a wet granulation process because the content uniformity of solifenacin or a pharmaceutically acceptable salt thereof is difficult to ensure via direct compression and also they tend to adhere to the punch during the compression process.

Accordingly, commercial formulations on the market such as Vesicare® containing solifenacin succinate are manufactured via a wet granulation process, and various methods have been suggested to improve the stability of such formulations. For example, KR Patent Application Publication No. 10-2007-0010132 discloses, as a method of preventing the time-based decomposition of a drug in solifenacin succinate-containing formulation, a method of controlling the percentage of the amorphous form in the formulation to a certain amount or lower, thereby preventing the time-based decomposition, or controlling the water content contained in the formulation during manufacture, heat treatment and/or humidity treatment after manufacture, thereby lowering the content of the amorphous form. Additionally, the above KR Patent Application Publication No. 10-2007-0010132 discloses that, at the time of manufacturing a formulation containing solifenacin or its salt, the amorphization of solifenacin can be prevented by using a binder such as polyethylene glycol (PEG), thereby manufacturing a formulation capable of inhibiting the time-based decomposition.

Additionally, KR Patent Application Publication No. 10-2007-0098889 discloses that, in manufacturing a granular pharmaceutical composition containing solifenacin or a pharmaceutically acceptable salt thereof, the stability of the main component can be secured by using a binder having a Tg of 174° C. or below.

As described above, due to the strong cohesiveness of solifenacin or a pharmaceutically acceptable salt thereof as a raw material and its instability during the formulation process, it is very difficult to select a suitable formulation method. The previously-suggested methods may provide a certain degree of stability but the water content contained in the granules during the wet granulation process is affected by various conditions during the manufacturing process such as reaction time, order of mixing, etc., and thus controlling the percentage of the amorphous form to a certain amount or lower by adjusting the water content is very unlikely to improve the stability of the formulation when this method is applied to large-scale production.

Additionally, in the case of manufacturing a formulation via a wet granulation method, the main components generally tend to exhibit time-based decomposition due to their interaction with water or organic solvents such as alcohol, and due to heat treatment for the purpose of removing the solvents.

Additionally, there are also limitations in the methods of preventing the time-based decomposition of solifenacin via selection and utilization of a specific binder for the wet granulation method due to the instability of the wet method. In particular, polyethylene oxide, which was suggested as one of the binders, has incompatibility with a strong oxidant (Handbook of Pharmaceutical excipients, 4th edition), and in addition, when lactose or mannitol is mixed with polyethylene oxide, the release behavior of the drug may vary over the course of its storage life, and thus its incompatibility was disclosed by a publication released by DOW company during the CRS conference in 2008 (KR Patent Application Publication No. 10-2012-0093500). Accordingly, considering that polyethylene oxide limits the selectable scope of the main excipients, with the combined use of polyethylene oxide is not desirable.

Therefore, there is still a high demand for the development of a novel preparation capable of preventing the time-based decomposition of solifenacin or its salt while also providing easy control over the preparation process in a commercial production environment.

DISCLOSURE

Technical Problem

Accordingly, the present invention has been made keeping in mind the above problems occurring in the prior art, and an objective of the present invention is to provide a preparation capable of preventing the time-based decomposition of solifenacin or a pharmaceutically acceptable salt thereof while also providing easy control over the preparation process in a commercial production environment.

Additionally, another objective of the present invention is to provide a preparation which can be manufactured via direct compression instead of a wet granulation process, and a method of manufacturing the same.

Technical Solution

In order to accomplish the above objectives, the present invention provides a solifenacin preparation comprising solifenacin or a pharmaceutically acceptable salt thereof, an antioxidant, and a binder.

As used herein, the term 'solifenacin' refers to a compound with the chemical name of (1R,3'R)-3'-quinuclidinyl-1-phenyl-1,2,3,4-tetrahydro-2-isoquinoline carboxylate [IUPAC name: 1-azabicyclo[2.2.2]oct-3-yl (1R)-1-phenyl-3,4-dihydro-1H-isoquinoline-2-carboxylate] as represented by Chemical Formula 1 below.

[Chemical Formula 1]

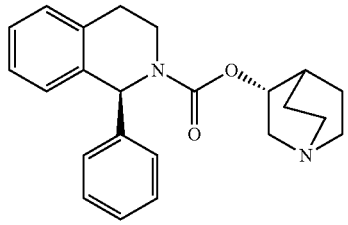

Solifenacin has been reported to have an excellent selective antagonistic action against muscarinic M3 receptors, and also is effective as a therapeutic agent for the prevention and treatment of urosis such as nervous pollakiuria, neurogenic bladder, nocturnal enuresis, unstable bladder, bladder contracture or chronic cystitis, and respiratory diseases such as chronic obstructive pulmonary disease, chronic bronchitis, asthma, rhinitis, etc.

Additionally, as used herein, the term 'pharmaceutically acceptable salt' refers to an acid added salt with an inorganic acid such as hydrochloric acid, hydrobromic acid, hydriodic acid, sulfuric acid, nitric acid, phosphoric acid, etc. or an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid, etc.; or a quaternary ammonium salt. Among them, succinate of solifenacin is desirable as a commercial drug and it is also preferable because it can be considerably stabilized by the present invention.

The present invention relates to a solifenacin preparation capable of inhibiting the time-based decomposition of solifenacin or its pharmaceutically acceptable salt while also providing easy control over the preparation process in a commercial production environment. Due to the high cohesiveness of solifenacin, the conventional wet granulation method has been used for securing content uniformity, but the wet granulation method cannot fundamentally resolve the problem of solifenacin decomposition because of the high sensitivity of solifenacin to water. In this regard, the present invention includes an antioxidant and a binder as constituting components of the solifenacin preparation, and thus is capable of securing content uniformity by direct compression instead of a wet granulation method, and also of fundamentally resolving the problem of the decomposition of solifenacin, which is sensitive to water.

As used herein, the term 'antioxidant' refers to a substance which inhibits the decomposition of solifenacin in a pharmaceutical preparation, and specifically, butylhydroxytoluene or butylhydroxyanisol may be used. Preferably, the antioxidant is used in the amount from 0.01 part by weight to 0.04 part by weight relative to 1 part by weight of solifenacin or a pharmaceutically acceptable salt thereof. When the amount is less than 0.01 part by weight, the amount of the main degradation product of solifenacin (hereinafter referred to as F1) relative to the total amount of solifenacin as an active ingredient and the degradation products cannot be maintained at a level of 0.5% or less, whereas when it exceeds 0.04 part by weight it can be toxic to the human body.

According to an embodiment of the present invention (Examples 1 through 7), at the time of manufacturing the preparation via direct compression, when the preparation includes an antioxidant to maintain stability of solifenacin, the degradation products of solifenacin was significantly reduced.

As used herein, the term 'binder' refers to a substance which provides a binding force to a solifenacin preparation, in particular, hydroxypropyl cellulose, gums, hydroxypropyl methylcellulose, polyvinylpyrrolidone, low-substituted hydroxypropyl cellulose, starch, lactose and a hydrate thereof, microcrystalline cellulose and ethylcellulose may be used. More preferably, low-substituted hydroxypropyl cellulose may be used. The low-substituted hydroxypropyl cellulose (L-HPC) used in the present invention refers to hydroxypropyl cellulose containing from 5% to 16% of hydroxypropoxy group. Due to the water-insolubility of low-substituted hydroxypropyl cellulose, when it contacts an aqueous solution it tends to swell, thereby providing a binding force during the direct compression method. Additionally, due to the swelling phenomenon, it is expected to have the indirect function of a disintegrating agent. Additionally, L-HPC has different particle sizes depending on the substitution level and thus L-HPC having the desired particle size may be selected to provide a binding force in the direct compression method.

Preferably, the binder is contained in the amount from 0.4 part by weight to 10 parts by weight relative to 1 part by weight of solifenacin or a pharmaceutically acceptable salt thereof. When the binder is contained in an amount less than 0.4 part by weight, the binding force during the tableting process becomes too weak to allow compression, or the prepared products may have low hardness, resulting in tablet fracture during the manufacturing process or other tablet defects seriously compromising their merchantability, thereby lowering production efficiency. Additionally, when the binder content exceeds 10 parts by weight, the in vivo dissolution pattern of the drug may not meet the requirement of bioequivalence in comparison with the commercial tablet products on the market, thus lowering the practicability of the corresponding solifenacin-containing tablet. Additionally, the binder is preferably contained in the amount from 25 parts by weight to 300 parts by weight relative to 1 part by weight of the antioxidant. More preferably, the binder is contained in the amount from 50 parts by weight to 200 parts by weight relative to 1 part by weight of the antioxidant. When the content ratio of the binder and the antioxidant are not within the above ranges, the stability of solifenacin may not be guaranteed or the problems of the direct compression method, e.g., content uniformity variations, may not be resolved.

As described above, the addition of the antioxidant and the binder as the constituting components of the solifenacin preparation can prevent generation of related substances or impurities and allow the solifenacin preparation to be formulated via a direct compression method, and also can provide a dissolution pattern equivalent to those of the commercial products.

According to an embodiment of the present invention (Examples 8 through 11), the solifenacin preparation containing the antioxidant and the binder showed a significant decrease in its mass deviation even when manufactured via direct compression. Additionally, according to an embodiment of the present invention (Example 12), the solifenacin preparation containing the antioxidant and the binder showed a significant content uniformity similar to the level of preparations manufactured via a wet granulation method. From the above, it was confirmed that the addition of the antioxidant and the binder as constituting ingredients of the solifenacin preparation could solve the problems existing in the conventional solifenacin preparations manufactured via a wet granulation method.

Additionally, the solifenacin preparation may further include a pharmaceutically acceptable disintegrating agent, lubricant or coating agent insofar as the inclusion thereof would not alter the effects of the present invention. The coating agent may form a film layer on the external surface of the solifenacin preparation, e.g., a light-shielding film layer, a moisture-proofing film layer, a sugar film layer, etc. The external film layer is preferably formed by a water-soluble material. Examples of the material for forming the water-soluble film layer may include hydroxypropyl methylcellulose, hydroxypropyl cellulose, hydroxyethyl cellulose, cellulose acetate phthalate, ethylcellulose, methylcellulose, polymethacrylate, polyvinyl alcohol (Opadry®; Colorcon, USA), and mixtures thereof, but not limited thereto.

Additionally, considering the pharmaceutically acceptable daily dose of solifenacin or a pharmaceutically acceptable salt thereof, the amount of solifenacin or a pharmaceutically acceptable salt thereof contained in the solifenacin preparation may be from 0.01 mg to 100 mg, preferably from 0.5 mg to 50 mg, more preferably from 0.5 mg to 20 mg, most preferably from 0.5 mg to 10 mg.

Additionally, the present invention provides a method for manufacturing a solifenacin preparation comprising the following steps of:

mixing solifenacin or a pharmaceutically acceptable salt thereof, an antioxidant and a binder (step 1); and tableting the mixture (step 2).

Generally, it is highly likely that the manufacture of preparations with a smaller proportion of main components by a direct compression method may cause problems of weight deviation or content uniformity among tablets. In particular, in the case of a main component such as solifenacin which has low stability, factors related to the stability of the main components should also be considered and thus it is very difficult to find an optimal method of manufacturing a preparation suitable for the characteristics of solifenacin as a main component.

The present invention, by including the antioxidant and the binder, provides a stable composition not generating drug degradation products or causing a decrease of drug content even when employing the direct compression method, while meeting the standards for content uniformity prescribed in the Revision of the Regulatory Provision for Review of Request on Specifications and Test Procedures of Drugs (Notification No. 2007-47 of the Korean Ministry of Food and Drug Safety, Jul. 2, 2007) and the Korean Pharmacopoeia (10$^{th}$ Edition). The manufacture of a preparation by the direct compression method according to the present invention is simpler than that by the wet granulation method and is thus advantageous for a large-scale process. As such, the above method of manufacturing the solifenacin preparation is characterized in that it does not include a solvent.

Examples of the pulverizer used in the process for preparing a stable pharmaceutical composition containing solifenacin or a salt thereof may include a hammer mill, a ball mill, a jet miller, a colloid mill, a motor-driven mesh, an oscillator, a co-mill, etc., but may not be particularly limited, and any device or means capable of pulverizing from the conventional, pharmaceutical aspect may be used.

A mixing device for each component used subsequently to the pulverization may include a V-type mixer, a ribbon-type mixer, a container mixer, a high speed agitator mixer, etc., but may not be particularly limited, and any device or means capable of uniformly mixing each component from the conventional, pharmaceutical aspect may be used.

Examples of tablet press machines may include rotary tablet press machines, single tablet press machines, etc., but they are not particularly limited, and any conventional pharmaceutical device or means capable of manufacturing compressed products (more appropriately, tablets) will be sufficient.

Advantageous Effects

According to the present invention, a solifenacin preparation containing solifenacin or a pharmaceutically acceptable salt thereof, an antioxidant, and a binder can be rapidly manufactured via a simplified direct compression method, and the thus-manufactured solifenacin preparation has excellent stability. Additionally, although the main components have high cohesiveness, the percentage of the main components in the preparation is low, and the preparation is manufactured via a direct compression method, the preparation, by including the antioxidant and the binder, is advantageous in that it has excellent content uniformity and is free of problems of weight deviation.

MODE FOR INVENTION

Figure 1A:
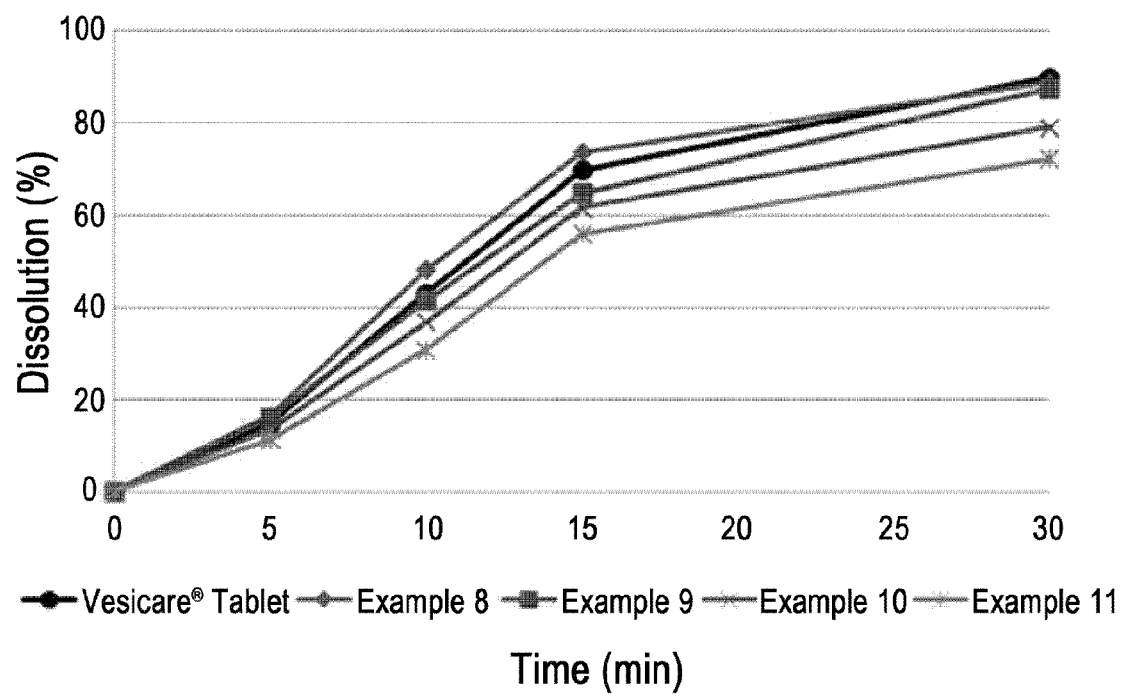
FIG. 1A and FIG. 1B respectively show the results of a dissolution test between the compositions of Examples 8 through 11 according to the present invention and the control drug (Vesicare® tablet), and the results of a dissolution test between the composition of Example 12, the composition of Comparative Example 3 and the control drug (Vesicare® tablet).

The present invention will be explained in greater detail through the following examples and experimental examples as set forth herein below, but they are disclosed for illustrative purposes only and are not to be construed as limiting the scope of the limit of the present invention.

EXAMPLE 1

For the manufacture of tablets, 16.65 g of solifenacin succinate, 0.5 g of butylhydroxytoluene, and 100.0 g of lactose were mixed by trituration and then filtered through a 30-mesh sieve (trituration mixing-1). Subsequently, 50.0 g of microcrystalline cellulose and 325.35 g of lactose hydrate were mixed, and filtered through a 30-mesh sieve (trituration mixing-2).

The trituration mixtures 1 and 2 were mixed in a 1 kg mixer (erweka AR 402/cubemixer) at 200 rpm for 15 minutes, and the resulting mixture was lubricated and mixed with 7.5 g of magnesium stearate, filtered through a 30-mesh sieve, and then formed into circular tablets using a single tablet press machine (erweka AR 401). The content of each component of the thus-obtained tablets is shown in Table 1 below.

TABLE 1

| Mixing Purpose | Composition (grade) | Weight % per Tablet |
|---|---|---|
| Excipient | lactose | 20.00 |
| Active Ingredient | solifenacin succinate | 3.33 |
| Disintegrating Agent | microcrystalline cellulose | 10.00 |
| Excipient | lactose hydrate | 65.07 |
| Antioxidant | butylhydroxytoluene | 0.10 |
| Lubricant | magnesium stearate | 1.50 |
| | Total Weight (%) | 100.00 |

EXAMPLES 2 THROUGH 7 AND COMPARATIVE EXAMPLE 1

In order to evaluate the degree of generation of related substances or impurities, or unknown materials by the addition of an antioxidant in the composition, tablets with the compositions of Examples 2 through 7 and Comparative Example 1 were manufactured.

For the manufacture of tablets with the compositions of Examples 2 through 7 and Comparative Example 1, 16.65 g of solifenacin succinate, butylhydroxytoluene (varying from 0.25 g to 0.5 g depending on Examples 2 through 7), 100.0 g of lactose hydrate and 50.0 g of microcrystalline cellulose were mixed by trituration, and then filtered through a 30-mesh sieve (trituration mixing-1). Subsequently, 100.0 g of microcrystalline cellulose and lactose hydrate (varying from 212.35 g to 212.85 g depending on Example 2 through 7 and Comparative Example 1), and then filtered through a 30-mesh sieve (trituration mixing-2).

The trituration mixtures 1 and 2 were mixed in a 1 kg mixer (erweka AR 402/cubemixer) at 200 rpm for 15 minutes, and the resulting mixture was lubricated and mixed with 7.5 g of magnesium stearate, filtered through a 30-mesh sieve, and then formed into circular tablets using a single tablet press machine (erweka AR 401). The thus-completed core tablets were coated with Opadry® (yellow, opadry 03B52293). The content of each component of the thus-obtained tablets is shown in Table 2 below.

TABLE 2

| Composition | Ex. 2 | Ex. 3 | Ex. 4 | Ex. 5 | Ex. 6 | Ex. 7 | Comp. Ex. 1 |
|---|---|---|---|---|---|---|---|
| Lactose | 20.00 | 20.00 | 20.00 | 20.00 | 20.00 | 20.00 | 20.00 |
| Solifenacin Succinate | 3.33 | 3.33 | 3.33 | 3.33 | 3.33 | 3.33 | 3.33 |
| Microcrystalline Cellulose (Trituration mixing-1) | 10.00 | 10.00 | 10.00 | 10.00 | 10.00 | 10.00 | 10.00 |
| Microcrystalline Cellulose (Trituration mixing-2) | 20.00 | 20.00 | 20.00 | 20.00 | 20.00 | 20.00 | 20.00 |
| Lactose Hydrate | 42.47 | 42.52 | 42.56 | 42.47 | 42.52 | 42.56 | 42.57 |
| Butylhydroxytoluene | 0.10 | 0.05 | 0.01 | — | — | — | — |
| Butylhydroxyanisol | — | — | — | 0.10 | 0.05 | 0.01 | — |
| Magnesium Stearate | 1.50 | 1.50 | 1.50 | 1.50 | 1.50 | 1.50 | 1.50 |
| Opadry ® (Yellow) | 2.60 | 2.60 | 2.60 | 2.60 | 2.60 | 2.60 | 2.60 |
| Total Weight (%) | 100 | 100 | 100 | 100 | 100 | 100 | 100 |

EXAMPLES 8 THROUGH 12 AND COMPARATIVE EXAMPLES 2 AND 3

In order to evaluate content uniformity and dissolution pattern of preparations according to the present invention, tablets with the compositions of Example 8 through 11 and Comparative Example 2 were manufactured.

16.65 g of solifenacin succinate, 0.5 g of butylhydroxytoluene, low-substituted hydroxypropyl cellulose (varying from 0.0 g to 150.0 g depending on the respective composition of Examples 8 through 11 and Comparative Example 2) and 95.0 g of isomalt were mixed by trituration, and filtered through a 30-mesh sieve (trituration mixing-1).

Subsequently, 10.0 g of hydrophobic colloidal silicon dioxide and lactose hydrate (varying from 207.35 g to 357.35 g depending on Examples 8 through 11 and Comparative Example 2) were mixed, and filtered through a 30-mesh sieve (trituration mixing-2).

The trituration mixtures 1 and 2 were mixed in a 1 kg mixer (erweka AR 402/cubemixer) at 200 rpm for 15 minutes, and the resulting mixture was lubricated and mixed with 7.5 g of magnesium stearate, filtered through a 30-mesh sieve, and then formed into circular tablets using a single tablet press machine (erweka AR 401). The thus-completed core tablets were coated with Opadry® (yellow, opadry 03B52293). The content of each component of the thus-obtained tablets is shown in Table 3 below.

TABLE 3

| Composition | Ex. 8 | Ex. 9 | Ex. 10 | Ex. 11 | Comp. Ex. 2 |
|---|---|---|---|---|---|
| Solifenacin Succinate | 3.33 | 3.33 | 3.33 | 3.33 | 3.33 |
| Butylhydroxytoluene | 0.10 | 0.10 | 0.10 | 0.10 | 0.10 |
| Hydrophobic Colloidal Silicon Dioxide | 2.00 | 2.00 | 2.00 | 2.00 | 2.00 |
| Low-Substituted Hydroxypropyl Cellulose | 5.00 | 10.00 | 20.00 | 30.00 | 0.00 |
| Isomalt | 19.00 | 19.00 | 19.00 | 19.00 | 19.00 |
| Lactose Hydrate | 66.47 | 61.47 | 51.47 | 41.47 | 71.47 |

TABLE 3-continued

| Composition | Ex. 8 | Ex. 9 | Ex. 10 | Ex. 11 | Comp. Ex. 2 |
|---|---|---|---|---|---|
| Magnesium Stearate | 1.50 | 1.50 | 1.50 | 1.50 | 1.50 |
| Opadry ® (Yellow) | 2.60 | 2.60 | 2.60 | 2.60 | 2.60 |
| Total Weight (%) | 100 | 100 | 100 | 100 | 100 |

Additionally, for the manufacture of tablets according to Example 12 and Comparative Example 3, 16.65 g of solifenacin succinate, 0.5 g of butylhydroxytoluene, low-substituted hydroxypropyl cellulose (varying from 0.0 g to 15.0 g depending on Example 12 and Comparative Example 3), lactose hydrate (varying from 18.35 g to 33.35 g depending on Example 12 and Comparative Example 3) and 33.35 g of isomalt were mixed by trituration, and filtered through a 30-mesh sieve (trituration mixing-1).

Subsequently, 5.0 g of hydrophobic colloidal silicon dioxide and 388.15 g of lactose were mixed and filtered through a 30-mesh sieve (trituration mixing-2).

The trituration mixtures 1 and 2 were mixed in a 1 kg mixer (erweka AR 402/cubemixer) at 200 rpm for 15 minutes, and the resulting mixture was lubricated and mixed with 10.0 g of sodium stearyl fumarate, filtered through a 30-mesh sieve, and then formed into circular tablets using a single tablet press machine (erweka AR 401). The thus-completed core tablets were coated with Opadry® (yellow, opadry 03B52293). The content of each component of the thus-obtained tablets is shown in Table 4 below.

TABLE 4

| Composition | Ex. 12 | Comp. Ex. 3 |
|---|---|---|
| Lactose Hydrate | 3.67 | 6.67 |
| Hydrophobic Colloidal Silicon Dioxide | 1.0 | 1.0 |
| Solifenacin Succinate | 3.33 | 3.33 |
| Low-Substituted Hydroxypropyl Cellulose | 3.00 | — |
| Butylhydroxytoluene | 0.10 | 0.10 |
| Isomalt | 6.67 | 6.67 |
| Lactose | 77.63 | 77.63 |
| Sodium Stearyl Fumarate | 2.0 | 2.0 |
| Opadry ® (Yellow) | 2.60 | 2.60 |
| Total Weight (%) | 100 | 100 |

EXAMPLE 13

In order to evaluate the dissolution of solifenacin succinate-containing preparations with different constitutional contents of solifenacin succinate, tablets with the composition of Example 13 were manufactured. The manufacturing process was the same as in Example 12, and the content of each component of the thus-obtained tablets is shown in Table 5 below.

TABLE 5

| Composition | Ex. 13 |
|---|---|
| Solifenacin succinate | 6.49 |
| Butylhydroxytoluene | 0.10 |
| Hydrophobic colloidal silicon dioxide | 2.92 |
| Low-substituted hydroxypropyl cellulose | 2.92 |
| Isomalt | 19.48 |
| Lactose hydrate | 64.03 |

TABLE 5-continued

| Composition | Ex. 13 |
|---|---|
| Magnesium stearate | 1.46 |
| Opadry ® (pink) | 2.60 |
| Total weight (%) | 100 |

EXPERIMENTAL EXAMPLE 1

Evaluation of Stability According to Composition of Preparations

Solifenacin succinate-containing preparations manufactured in Examples 1 through 7 and Example 8 containing a binder were packed in PVC, PVDC, and HDPE containers conventionally used in the art, stored under severe stability conditions (60° C./relative humidity 80%), and the change in related substances at initial stage, after 1 week, 2 weeks, and 4 weeks of storage were analyzed. Vesicare® 5 mg coated tablets on the market were used as a control drug, and stability test was performed under the same condition.

The standard of related substances or impurities in solifenacin succinate as a raw material was applied to this Example, and the detailed standard and items are shown in Table 6 below.

TABLE 6

| Related Substances or Impurities | Standard |
|---|---|
| YM-64250 (+)-(1S,3'R)-1'-oxidoquinuclidin-3'-yl-1-phenyl-1,2,3,4-tetrahydroisoquinoline-2-carboxylate | ≤1.1% |
| YM 217880 (+)-(R)-quinuclidin-3-yl [2-(2-benzoylphenyl)ethyl]carbamate | ≤0.5% |
| Unknown Related Substances or Impurities | ≤0.2% |
| Total of Related Substances or Impurities | ≤2.0% |

The change in the related substances or impurities was analyzed via high performance chromatography (Agilent) and the HPLC conditions used are as follows.

Detector: UV spectrophotometer (wavelength for measurement: 215 nm)

Column: XBridge™ C18, 150×4.6 mm, 5.0 μm or a column equivalent thereof

Flow rate: 1.0 mL/min

Column temperature: a constant temperature around 35° C.

Amount of injection: 20 μL

Range of measurement: 1) for 40 minutes after injecting a test solution 2) for 20 minutes after injecting a standard solution Mobile phase: buffer solution*/methanol=35/65

Diluent: mobile phase

*buffer solution: 3.4 g of dipotassium monohydrogen phosphate was well dissolved in 1000 mL of water, added with 1.0 mL of trifluoroacetic acid, and adjusted to a pH of 7.5 by using triethylamine. The resulting solution was filtered through a 0.45 μm filter and deaerated to be used.

The evaluation results on the stability are shown in Table 7 below.

TABLE 7

| Category | Related Substances or Impurities | Standard | Initial stage | Under Severe Stress Condition for 1 Week | | | Under Severe Stress Condition for 2 weeks | | | Under Severe Stress Condition for 4 weeks | | |
|---|---|---|---|---|---|---|---|---|---|---|---|---|
| | | | | Bottle (%) | PVC (%) | PVDC (%) | Bottle (%) | PVC (%) | PVDC (%) | Bottle (%) | PVC (%) | PVDC (%) |
| Control Drug (Vesicate ®, 5 mg) | YM-64250 | ≤1.1% | ND* | 0.59 | 1.07 | 0.48 | 1.03 | 1.33 | 0.59 | 1.12 | 1.63 | 0.57 |
| | YM 217880 | ≤0.5% | ND | ND | 0.55 | 0.25 | 0.71 | 0.96 | 0.43 | 0.80 | 0.96 | 1.78 |
| | Other | ≤0.2% | ND | ND | ND | ND | ND | 0.13 | ND | ND | 0.28 | ND |
| | respective impurities total | ≤2% | ND | 0.59 | 1.62 | 0.73 | 1.74 | 2.42 | 1.02 | 1.52 | 2.87 | 2.35 |
| Ex. 1 | YM-64250 | ≤1.1% | ND | ND | ND | ND | 0.05 | 0.38 | 0.36 | 0.07 | 0.74 | 0.75 |
| | YM 217880 | ≤0.5% | ND | ND | ND | ND | 0.01 | 0.16 | 0.16 | 0.03 | 0.36 | 0.37 |
| | Other | ≤0.2% | ND | ND | ND | ND | ND | ND | ND | ND | ND | ND |
| | respective impurities total | ≤2% | ND | ND | ND | ND | 0.06 | 0.54 | 0.52 | 0.10 | 1.1 | 1.12 |
| Ex. 2 | YM-64250 | ≤1.1% | ND | ND | ND | ND | 0.14 | ND | ND | 0.67 | ND | ND |
| | YM 217880 | ≤0.5% | ND | ND | ND | ND | 0.26 | ND | ND | 0.61 | ND | ND |
| | Other- | ≤0.2% | ND | ND | ND | ND | ND | ND | ND | ND | ND | ND |
| | respective impurities total | ≤2% | ND | ND | ND | ND | 0.4 | ND | ND | 1.28 | ND | ND |
| Ex. 3 | YM-64250 | ≤1.1% | ND | ND | ND | ND | ND | ND | ND | 0.59 | ND | ND |
| | YM 217880 | ≤0.5% | ND | ND | ND | ND | ND | 0.12 | ND | 0.81 | ND | ND |
| | Other | ≤0.2% | ND | ND | ND | ND | ND | ND | ND | ND | ND | ND |
| | respective impurities total | ≤2% | ND | ND | ND | ND | ND | 0.12 | ND | 1.4 | ND | ND |
| Ex. 4 | YM-64250 | ≤1.1% | ND | 0.24 | 0.4 | ND | ND | 0.25 | ND | 0.67 | 0.57 | 0.69 |
| | YM 217880 | ≤0.5% | ND | 0.08 | 0.17 | ND | ND | 0.43 | 0.11 | 0.78 | 0.26 | 0.42 |
| | Other | ≤0.2% | ND | ND | ND | ND | ND | ND | ND | ND | ND | ND |
| | respective impurities total | ≤2% | ND | 0.32 | 0.31 | ND | ND | 0.68 | 0.11 | 1.45 | 0.83 | 1.11 |
| Ex. 5 | YM-64250 | ≤1.1% | ND | ND | ND | ND | ND | ND | ND | ND | ND | ND |
| | YM 217880 | ≤0.5% | ND | ND | ND | ND | ND | ND | ND | ND | ND | ND |
| | Other | ≤0.2% | ND | ND | ND | ND | ND | ND | ND | ND | ND | ND |
| | respective impurities Total | ≤2% | ND | ND | ND | ND | ND | ND | ND | ND | ND | ND |
| Ex. 6 | YM-64250 | ≤1.1% | ND | ND | ND | ND | ND | ND | ND | ND | ND | ND |
| | YM 217880 | ≤0.5% | ND | ND | ND | ND | ND | ND | ND | ND | ND | ND |
| | Other | ≤0.2% | ND | 0.03 | ND | ND | ND | ND | ND | ND | ND | ND |
| | respective impurities Total | ≤2% | ND | 0.03 | ND | ND | ND | ND | ND | ND | ND | ND |
| Ex. 7 | YM-64250 | ≤1.1% | ND | ND | ND | ND | 0.06 | ND | ND | ND | ND | ND |
| | YM 217880 | ≤0.5% | ND | ND | ND | ND | 0.17 | ND | ND | ND | ND | ND |
| | Other | ≤0.2% | ND | 0.03 | ND | ND | ND | ND | ND | ND | ND | ND |
| | respective impurities Total | ≤2% | ND | 0.03 | ND | ND | 0.25 | ND | ND | ND | ND | ND |
| Ex. 8 | YM-64250 | ≤1.1% | ND | ND | ND | ND | 0.04 | 0.27 | 0.24 | 0.07 | 0.35 | 0.37 |
| | YM 217880 | ≤0.5% | ND | ND | ND | ND | 0.02 | 0.11 | 0.12 | 0.05 | 0.41 | 0.39 |
| | Other | ≤0.2% | ND | ND | ND | ND | ND | 0.01 | ND | 0.05 | 0.02 | |
| | respective impurities Total | ≤2% | ND | ND | ND | ND | 0.07 | 0.39 | 0.36 | 0.12 | 0.81 | 0.78 |
| Comp. Ex. 1 | YM-64250 | ≤1.1% | ND | 0.23 | 1.35 | 0.42 | 0.36 | 1.36 | 0.94 | 1.41 | 1.88 | 1.08 |
| | YM 217880 | ≤0.5% | ND | 0.40 | 1.06 | 0.35 | 0.56 | 1.21 | 0.80 | 0.89 | 1.37 | 1.10 |
| | Other | ≤0.2% | ND | 0.49 | 0.13 | ND | ND | ND | ND | ND | 0.29 | ND |
| | respective impurities Total | ≤2% | ND | 1.12 | 2.54 | 0.77 | 0.92 | 2.57 | 1.74 | 2.3 | 3.25 | 2.18 |

In the case of the preparation of Example 1, although it was a core tablet, all of its contents and the levels of related substances satisfied the standard requirement and remained stable until the 4$^{th}$ week of severe stress conditions regardless of their packing materials. However, in the case of the control drug, the related substance YM-64250 failed to meet the standard in PVC packing (under 1 to 4 weeks of severe stress conditions) and HDPE (4 weeks) materials, and the related substance YM-217880 failed to meet the standard in PVC packing (under 1 to 4 weeks of severe stress conditions) HDPE (2 and 4 weeks), and PVDC (4 weeks) materials.

In the case of the preparation of Example 2, the presence of the related substance YM-64250 was detected in HDPE container until the $2^{nd}$ and $4^{th}$ week of the severe stress conditions, but the detected level was lower than that of control drugs on the market and satisfied the standard requirement.

Temperature of Dissolution medium: 37.5° C.±0.5

Dissolution Apparatus: UV Spectrophotometer (wavelength for measurement: 210 nm).

Column: Develosil ODS-UG-5 (150 mm×4.6 mm ID, Nomura Chemical Co., Ltd.) or a column equivalent thereof Column temperature: 40° C.

Mobile phase: 0.05 mol/L potassium phosphate buffer (pH 6.0)/acetonitrile mixture (65:35)

Flow rate: 1.0 mL/min (adjusted to maintain the retention time of solifenacin to be between 7 min to 11 min)

Test Period: About 12 min

As a result of the experiment, the dissolution rate of each preparation in the phosphate buffer at pH 6.8 was as shown in Table 8.

TABLE 8

| Dissolution Time (min) | Ex. 8 | Ex. 9 | Ex. 10 | Ex. 11 | Comp. Ex. 2 | Control Drug |
| --- | --- | --- | --- | --- | --- | --- |
| 5  | 22.5 ± 5.4 | 18.4 ± 4.7 | 15.9 ± 2.4 | 12.1 ± 6.2 | 29.8 ± 1.4  | 26.3 ± 4.0 |
| 10 | 43.8 ± 2.8 | 39.9 ± 2.3 | 37.5 ± 2.2 | 30.4 ± 2.9 | 56.7 ± 9.8  | 50.9 ± 5.8 |
| 15 | 64.5 ± 2.1 | 60.7 ± 2.2 | 58.5 ± 1.2 | 49.7 ± 3.8 | 83.6 ± 8.7  | 69.6 ± 8.1 |
| 30 | 84.1 ± 1.6 | 81.1 ± 1.6 | 77.6 ± 0.8 | 68.6 ± 4.4 | 93.8 ± 5.1  | 89.6 ± 2.5 |
| 45 | 89.4 ± 1.1 | 87.3 ± 1.5 | 84.7 ± 1.1 | 82.8 ± 3.1 | 107.5 ± 5.0 | 93.7 ± 2.4 |

Overall, it was confirmed that antioxidants, butylhydroxytoluene and butylhydroxyanisol used in Examples 1 through 7 improved the stability of solifenacin succinate. Additionally, in the preparation of tablets with the composition of Example 8 containing an antioxidant and a binder, it was also confirmed that the level of the related substances satisfied the standard requirement.

However, in the case of the preparation of Comparative Example 1 and the control drug not containing an antioxidant, the levels of the related substances or impurities, or the unknown related substances of solifenacin succinate were shown very high. Accordingly, it was confirmed that the solifenacin succinate-containing preparations according to the present invention were very effectively prevented from generating the related substances and also had an excellent stability compared to that of the control drug.

EXPERIMENTAL EXAMPLE 2

Evaluation of Dissolution Rate According to Compositions of Preparations

The dissolution rates of the solifenacin succinate-containing preparations according to the present invention were evaluated by comparing with those of the control drug (Vesicare®, 5 mg). The conditions applied in the evaluation of the dissolution rates are as follows.

Manufacturer of Dissolution Apparatus and Test solution sampling Apparatus: Agilent technologies Model name of Dissolution Apparatus: 708-DS Model name of Test solution sampling Apparatus: Dissolution sampling station Test solution sampling method: Auto sampling according to time passage Dissolution method: the Korean Pharmacopoeia ($10^{th}$ Edition), the $2^{nd}$ method (paddle speed: 50 rpm)

Time for collecting test solution: 5, 10, 15, 30 (and 45 min)

Number of tested materials: 4 tablets

Dissolution medium: Purified water and pH 6.8 phosphate buffer

From the results of Examples 8 through 11, it was confirmed that the greater the amount of a binder, the lower the dissolution rate. In the case of the preparation of tablets according to the composition of Example 11, its dissolution rate, at 30 minutes, fell short of 80% of that of the control drug, the drug on the market, and thus it is not suitable for a release profile of a solifenacin-containing preparation, which requires a fast release, in terms of biological equivalence (according to the Notification No. 2013-201 of the Korean Ministry of Food and Drug Safety, when the average dissolution rate of a drug on the market (reference drug) reaches 85% between 15 min and 30 min, if the average dissolution rate of a drug to be compared (test drug) is within that of the reference drug ±15% at two different time points where the average dissolution rate of the reference drug is around 60% and 85%, respectively, they can be determined as having equivalence). Additionally, it is also not suitable considering there is a large deviation in terms of average dissolution rate.

When a binder was not added at all (Comparative Example 2), there was a large deviation in terms of average dissolution rate and thus a stable in vivo dissolution of the preparation cannot be expected.

EXPERIMENTAL EXAMPLE 3

Evaluation of Dissolution Pattern According to Compositions of the Preparations

The dissolution patterns of the tablets manufactured via direct compression in Examples 8 through 11 and Comparative Example 2 were observed in purified water and compared with that of the control drug. The results are shown in FIG. 1A. The conditions for the evaluation of the dissolution were the same as provided in Experimental Example 2.

The preparations of Examples 8 through 10 and Comparative Example 2 had dissolution rates of between 54.8% and 84.8% at the 15 min determining point, and between 74.9% and 104.9% at the 30 min determining point, thus being considered to be equivalent with that of the drug on the market (according to the Notification No. 2013-201 of the Korean Ministry of Food and Drug Safety, when the average dissolution rate of a drug on the market (reference drug) reaches 85% between 15 min and 30 min, if the average dissolution rate of a drug to be compared (test drug) is within that of the reference drug ±15% at two different time points where the average dissolution rate of the reference drug is around 60% and 85%, respectively, they can be determined as having equivalence).

Meanwhile, the preparation of Example 11 showed a dissolution rate of 55.9%, thus being equivalent, but at the 30 min determining point, it showed a dissolution rate of 72.2%, which was lower than the equivalent range of ±15%. Accordingly, the preparation is not suitable for use as a solifenacin-containing preparation with regard to biological equivalence.

Figure 1B:
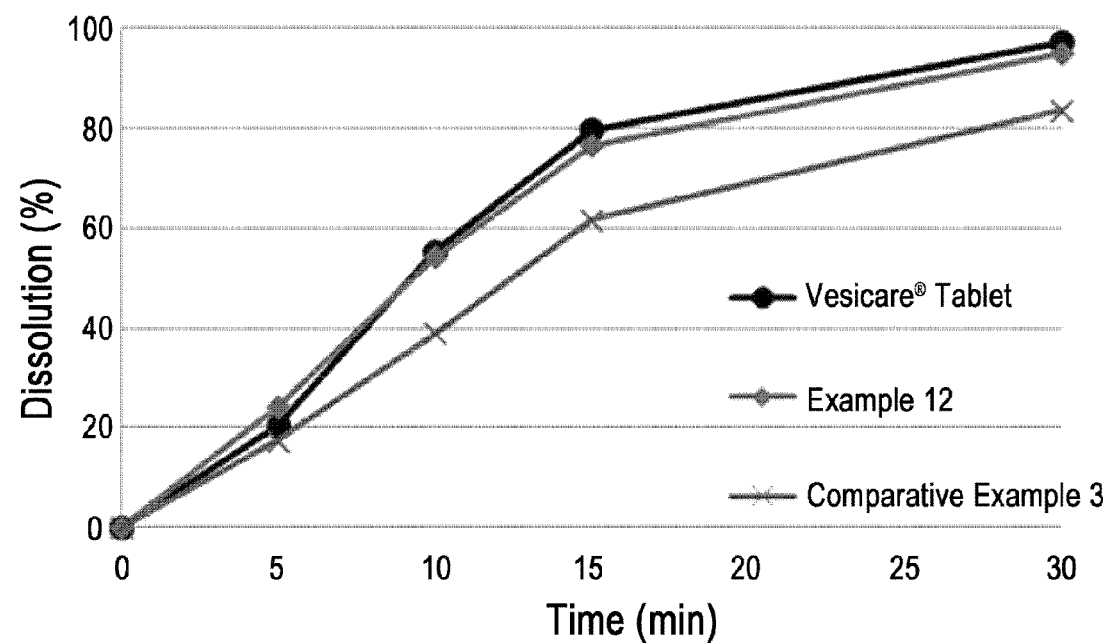

The dissolution patterns of the preparations of Example 12 and Comparative Example 3 were evaluated by comparing them with those of the control drug. The results are shown in FIG. 1B. The conditions for the evaluation of the dissolution were the same as used in Experimental Example 2.

As a result of the evaluation, the preparation of Example 12 showed a dissolution profile equivalent to that of the control drug. However, the dissolution rate of the preparation of Comparative Example 3 was outside of the range that could be considered as determining equivalence to that of the control drug.

Figure 2:
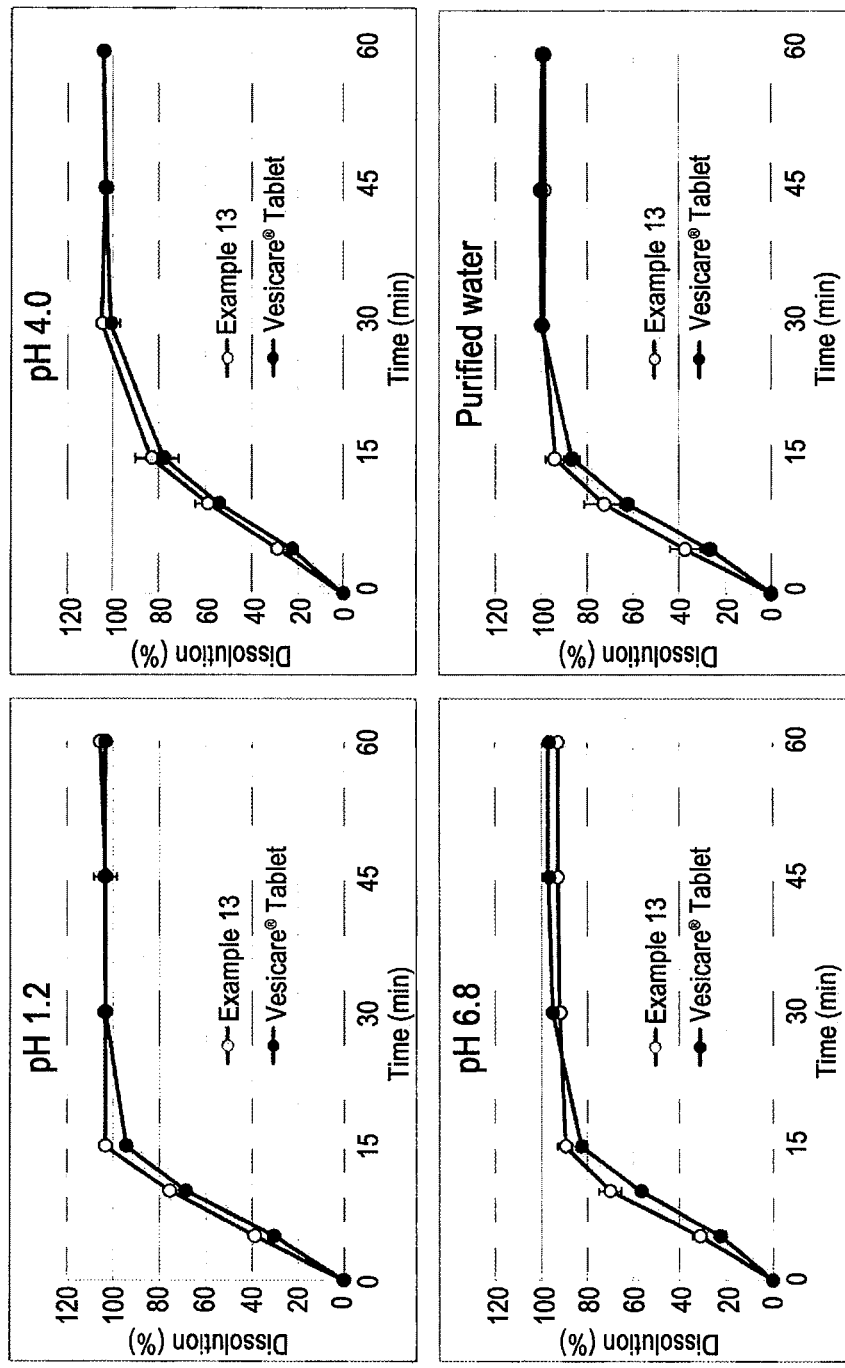
FIG. 2 shows the results of a dissolution test between the composition of Example 13 according to the present invention and the control drug (Vesicare® tablet, 10 mg).

The dissolution pattern of the preparation of Example 13, which contains 10 mg of solifenacin, was evaluated by comparing it with that of the control drug, and was shown to have an equivalent level of dissolution to that of the control drug (FIG. 2). The condition for the evaluation of the dissolution was the same suggested in Experimental Example 2.

As a result of the evaluation, it was confirmed that the dissolution pattern of the preparation containing 10 mg of solifenacin according to the present invention is equivalent to that of the control drug.

EXPERIMENTAL EXAMPLE 4

Evaluation of Content Uniformity and Degree of Disintegration

Mass deviation and degree of disintegration among various compositions in Examples were evaluated by comparison, and the results are shown in Table 9 below. The preparations of Examples 8 through 11 and Comparative Example 2 were all manufactured to have the same hardness.

TABLE 9

| Evaluation Item | Ex. 8 | Ex. 9 | Ex. 10 | Ex. 11 | Comp. Ex. 2 |
|---|---|---|---|---|---|
| Hardness (KP) | 7 ± 1 | 7 ± 1 | 7 ± 1 | 8 ± 3 | 7 ± 4 |
| Mass Deviation (%) | 0.59 | 0.59 | 1.02 | 3.34 | 7.03 |
| Degree of Disintegration (min) | 4 ± 1 | 4 ± 1.5 | 6 ± 1 | 12 ± 2.5 | 5 ± 3.8 |
| Disintegration Time in a Medium at pH 6.8 (min) | 9 ± 1 | 10 ± 2 | 11 ± 3 | 21 ± 4 | 12 ± 7 |

The preparation of Example 11, to which a binder was added in the amount of at least 30%, showed a larger tableting deviation compared with those in other Examples, and also showed a larger mass deviation compared with those in other Examples. In the case of Comparative Example 2, which had no binder added at all, the deviation relative to individual weight after tableting was shown as large as being around average weight ±7%.

As a result of evaluating the degree of disintegration and disintegration time in a phosphate buffer medium at pH 6.8 according to the types prepared, it was confirmed that the preparation of Example 11 requires a considerable amount of time for its dissolution. This implies that the preparation failed to show a desirable dissolution pattern considering that solifenacin succinate, as a main component, should be fast-released for rapid therapeutic action.

Table 10 below shows the results of evaluation by comparison of content uniformity of solifenacin succinate contained per each tablet of the preparations in Example 12 and Comparative Example 3 relative to the control drug on the market (Vesicare® tablet). The content uniformity test was performed according to the Content Uniformity Test Method of the General Test Methods in the Korean Pharmacopoeia (KP 10).

1) Diluent: a mixed solution of water/acetonitrile=7/3

2) Preparation of Test Solution: About one tablet was added into a 20 mL flask, filled up with the diluent up to about 80%, agitated while occasionally shaking the flask until the test material was disintegrated, and cooled at room temperature. The resultant was added with the diluent to 20 mL and filtered through a 0.45 μm PVDF membrane filter to obtain a test solution.

3) Preparation of Standard Solution: 50 mg of a reference standard of solifenacin succinate was accurately added into a 100 mL flask and line-marked with the diluent to obtain a standard solution.

4) Operation and Calculation: 10 μL each of the test solution and the standard solution were subjected to the liquid chromatography under the same operating condition as in the content test, and the amount of solifenacin succinate was calculated via the following equation.

$$\text{Content of solifenancin succinate (\%)} = \frac{A_T}{A_S} \times \frac{W_S}{C} \times \frac{P}{D} \quad \text{5) Equation}$$

$A_T$: Peak area of solifenacin succinate in the chromatogram of a test solution $A_S$: Peak area of solifenacin succinate in the chromatogram of a standard solution $W_S$: Amount of collection of a reference standard of solifenacin succinate (mg)

C: Indicated amount of solifenacin succinate per one tablet of a drug (mg)

P: Purity of a reference standard of solifenacin succinate (%)

D: Dilution fold (5)

TABLE 10

| No. of Tests | Ex. 12 | Comp. Ex. 3 | Control Drug |
|---|---|---|---|
| Test - 1 | 98.80 | 101.26 | 100.50 |
| Test - 2 | 100.4 | 101.17 | 101.74 |
| Test - 3 | 100.8 | 95.95 | 98.63 |
| Test - 4 | 100.6 | 99.42 | 100.90 |
| Test - 5 | 101.9 | 98.10 | 99.66 |
| Test - 6 | 103.9 | 97.24 | 97.52 |

TABLE 10-continued

| No. of Tests | Ex. 12 | Comp. Ex. 3 | Control Drug |
|---|---|---|---|
| Test - 7 | 104.1 | 95.31 | 100.24 |
| Test - 8 | 100.1 | 96.46 | 99.69 |
| Test - 9 | 100.8 | 95.68 | 100.01 |
| Test - 10 | 100.0 | 96.46 | 101.68 |
| Mean | 101.1 | 97.71 | 100.06 |
| Standard Deviation | 1.70 | 2.21 | 1.30 |

As a result of the content uniformity test, it was confirmed that the preparation of Example 12 manufactured via a direct compression method by adding a binder had an equivalence in terms of preparation uniformity and content in an individual tablet to that of the control drug, and showed an improved result compared to the composition not using a binder (Comparative Example 3) (the recommended standard for solifenacin succinate content of the drugs on the market is in the range of from 93.0% to 105.0%).

From the above results, it was found that a simple application of the direct compression method can cause various problems in the tableting process such as insufficient filling into dies of a tablet press, a serious mass deviation due to separation of layers or polarization within the granulated materials mixed therein, content non-uniformity, sticking, capping, etc.

However, it was confirmed that the application of the compositions of the present invention enables the manufacture of preparations, which are expected to exhibit an in vivo dissolution at a degree equivalent to that of the control drug without any problems such as difficulty in tableting or mass deviation.

When the manufacture is performed using a high speed tableting machine, in order to evaluate the effect on the content of the main components, the composition of Example 12 was manufactured via high speed tableting, and the content of solifenacin succinate according to the tableting time was measured. The high speed tableting machine used was an 8-station Piccolo rotary tablet press (RIVA), wherein the turret was rotated at 25 rpm, and the tableted test materials were randomly collected at the predetermined time for measurement, and three tablets were selected therefrom and subjected to a test for the average content. The tablets were collected at initial time, 5, 10, 15, 30, 45, and 60 min, and the collection was stopped thereafter. The test results are shown in Table 11 below. The tablets manufactured via high speed tableting showed no difference in content compared to those manufactured by a single tableting machine.

TABLE 11

| Collection Time of Tableted Material | Test - 1 | Test - 2 | Test - 3 | Mean | Standard Deviation |
|---|---|---|---|---|---|
| Initial time | 100.6 | 100.7 | 99.7 | 100.3 | 0.5 |
| 5 min after high speed tableting | 100.3 | 101.0 | 99.8 | 100.4 | 0.6 |
| 10 min after high speed tableting | 101.6 | 99.9 | 97.5 | 99.7 | 2.1 |
| 15 min after high speed tableting | 98.2 | 99.2 | 100.7 | 99.4 | 1.3 |
| 30 min after high speed tableting | 99.4 | 100.3 | 97.9 | 99.2 | 1.2 |
| 45 min after high speed tableting | 102.7 | 104.0 | 101.3 | 103.3 | 0.9 |
| 60 min after high speed tableting (termination) | 102.2 | 97.5 | 98.3 | 99.3 | 2.5 |

The invention claimed is:

1. A solifenacin tablet prepared via direct compression, comprising solifenacin or a pharmaceutically acceptable salt thereof, an antioxidant, and a binder, wherein the binder is contained in the amount from 0.0292 part by weight to 0.3 part by weight relative to total weight of the tablet.

2. The solifenacin tablet of claim 1, wherein the antioxidant is contained in the amount from 0.01 part by weight to 0.04 part by weight relative to 1 part by weight of the solifenacin or a pharmaceutically acceptable salt thereof.

3. The solifenacin tablet of claim 1, wherein the antioxidant is butylhydroxytoluene or butylhydroxyanisol.

4. The solifenacin tablet of claim 1, wherein the binder is low-substituted hydroxypropyl cellulose.

5. The solifenacin tablet of claim 1, wherein the binder is contained in the amount from 25 parts by weight to 300 parts by weight relative to 1 part by weight of the antioxidant.

6. The solifenacin tablet of claim 5, wherein the binder is contained in the amount from 50 parts by weight to 200 parts by weight relative to 1 part by weight of the antioxidant.

7. The solifenacin tablet of claim 1, wherein the binder is contained in the amount from 0.4 part by weight to 10 parts by weight relative to 1 part by weight of the solifenacin or a pharmaceutically acceptable salt thereof.

8. The solifenacin tablet of claim 1, further comprising a disintegrating agent, a lubricant or a coating agent.

9. A method for manufacturing solifenacin tablet, comprising:
    mixing solifenacin or a pharmaceutically acceptable salt thereof, an antioxidant and a binder; and
    tableting the mixture via direct compression,
    wherein the binder is contained in the amount from 0.0292 part by weight to 0.3 part by weight relative to total weight of the tablet.

10. The method of claim 9, wherein the mixture does not comprise a solvent.

\* \* \* \* \*